US012569312B2

(12) United States Patent
Zhu et al.

(10) Patent No.: US 12,569,312 B2
(45) Date of Patent: Mar. 10, 2026

(54) MINIATURE SINGLE-PHOTON FLUORESCENCE MICROSCOPE IMPLANTATION DEVICE AND IMPLANTATION METHOD

(71) Applicant: SHENZHEN INSTITUTES OF ADVANCED TECHNOLOGY CHINESE ACADEMY OF SCIENCES, Shenzhen (CN)

(72) Inventors: Yingjie Zhu, Shenzhen (CN); Gaowei Chen, Shenzhen (CN); Shaolei Jiang, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 561 days.

(21) Appl. No.: 18/313,383

(22) Filed: May 8, 2023

(65) Prior Publication Data

US 2023/0270519 A1     Aug. 31, 2023

Related U.S. Application Data

(63) Continuation of application No. PCT/CN2021/137268, filed on Dec. 11, 2021.

(51) Int. Cl.
*A61B 90/14*        (2016.01)
*A61B 1/00*         (2006.01)

*A61B 1/002*        (2006.01)
*A61B 90/11*        (2016.01)
*G02B 21/00*        (2006.01)

(52) U.S. Cl.
CPC ................ *A61B 90/14* (2016.02); *A61B 1/00* (2013.01); *A61B 1/002* (2013.01); *A61B 90/11* (2016.02); *G02B 21/00* (2013.01); *A61B 2503/40* (2013.01)

(58) Field of Classification Search
CPC ..... G02B 13/0095; A61B 1/002; A61B 90/14; A61B 90/11; A61B 2503/40
See application file for complete search history.

(56) References Cited

U.S. PATENT DOCUMENTS

| | | | |
|---|---|---|---|
| 2005/0094260 A1 | 5/2005 | Tokuda et al. | |
| 2015/0366437 A1* | 12/2015 | Labrie .................. | A61B 5/0084 600/478 |
| 2017/0363849 A1 | 12/2017 | Doric et al. | |
| 2018/0296074 A1* | 10/2018 | Trulson .............. | A61B 1/00045 |

FOREIGN PATENT DOCUMENTS

| | | |
|---|---|---|
| CN | 111543956 A | 8/2020 |
| WO | 2012124092 A1 | 9/2012 |

* cited by examiner

*Primary Examiner* — Alexander P Gross

(57) ABSTRACT
A miniature single-photon fluorescence microscope implantation device and implantation method are disclosed. The implantation device includes: a clamp base defining a clamp slot; a clamp block; and a groove defined in a bottom surface of the clamp slot. An end of the clamp block includes a first protrusion, and a bottom surface of the groove vertically defines a through receiving hole.

16 Claims, 7 Drawing Sheets

MINIATURE SINGLE-PHOTON FLUORESCENCE MICROSCOPE IMPLANTATION DEVICE AND IMPLANTATION METHOD

CROSS-REFERENCE TO RELATED APPLICATIONS

This application is a continuation of co-pending International Patent Application Number PCT/CN2021/137268, filed on Dec. 11, 2021, the disclosure of which is incorporated herein by reference in its entirety.

TECHNICAL FIELD

The present application relates to the technical field of neurobiology, and more particularly relates to a miniature single-photon fluorescence microscope implantation device and implantation method.

BACKGROUND

Nowadays, in the field of neurobiology, various neural-electrical activity-dependent fluorescence carrier tools may be injected into an experimental target brain region of a mouse to intuitively observe the nerve cell activities in deep brain regions with the help of a miniature single-photon fluorescence microscope. To realize this technology, a lens adapted to the microscope needs to be assembled with a clamp groove used to fix the microscope. Because the microscope cannot be directly implanted in the deep brain region, a special cylindrical lens needs to be used in conjunction with the microscope to serve as an extension of the microscope lens for purposes of capturing the field of view in deep brain regions.

As an extension of the microscope lens, the end surface of the lens portion exposed outside the mouse skull should be absolutely parallel to the surface of the microscope lens to ensure its role as an extension, and an operating distance of 0.5 mm should be left between the lens and the microscope surface in order to function. To achieve an ideal working state of the miniature microscope, three technical problems need to be solved. First, precise implantation of the lens. In the field of neurobiology, there is a common experimental demand for implanting optical fibers into specific brain regions of mice. Generally, the gripping, fixing, and implantation of optical fibers may be performed by using a stereotaxic instrument with a matching joystick. The adaptive device for implanting optical fibers is relatively mature. However, due to the immature development of single-photon calcium imaging technology, there is no joystick suitable for the process of implanting the lens. At present, a relatively mature solution in the industry is one proposed by Thinker Tech Nanjing Biotech Co., Ltd. (hereinafter Thinker Tech), including mounting a resin frame holder on the basis of the joystick for implanting optical fibers. However, this method cannot solve the problem of the lens tilting back and forth during the clamping process, resulting in a cumbersome lens implantation process and a low success rate. The lens clamping solution of Thinker Tech is particularly illustrated in FIG. 2. After the lens is successfully implanted, it takes three weeks for the experimental animal to complete the expression of the injected tool virus before the second operation can be performed. The purpose of the second operation is to equip a miniature fluorescence microscope mount on the surface of the skull of the experimental animal. During this process, the upper and lower surfaces of the mount should be parallel to the bottom surface of the cylindrical lens to ensure that the surface of the fluorescence microscope lens is parallel to and coincident with the surface of the cylindrical lens after the fluorescence microscope lens is inserted into the mount, while a 0.5 mm gap is left between the lens surface of the fluorescence microscope lens and the surface of the cylindrical lens. Thinker Tech's solution includes designing a mount with no upper and lower bottoms and only four sides, as illustrated in FIG. 1, where one of the four sides defines a screw hole. After inserting the microscope lens into the mount, the fluorescence microscope lens is fixed to the mount by a bolt. The fluorescence microscope together with the mount is then held using a miniature microscope holder designed by Thinker Tech. Then alignment of the miniature fluorescence microscope lens with the cylindrical lens is performed using a stereotaxic instrument. After finding the ideal field of view of the fluorescence microscope, the head of the experimental animal and the fluorescence microscope assembled with the mount are kept still, and a photocurable resin is used to bond the mount to the surface of the skull of the experimental animal. Then the bolt in the mount is loosened and the fluorescence microscope is taken out, thereby completing the assembly of the mount. In formal experiments, the fluorescence microscope lens is inserted into the mount for microscopic imaging and observation. The entirety of the solution is illustrated in FIGS. 3 to 4. Because whether the four walls of the mount are perpendicular to the cylindrical lens surface directly determines whether the surface of the fluorescence microscope lens after entering the mount is parallel to the cylindrical lens surface, this operation requires adequate precision thus posing a great technical problem, and it also consumes a lot of time.

In sum, the following defects are present in the above prior art. First, two operations are required, namely the first lens implantation and the second installation of the miniature fluorescence microscope mount on the surface of the experimental animal skull. Both operations require the mouse to be anesthetized and fixed, and will cause additional impact on the animal and significant disturbance to the experiment. Second, in the prior art, it is needed to use a resin frame holder to clamp the lens for implantation, which is accompanied by the risk of damage to the lens. The lens is easy to tilt during the clamping process, leading to inaccurate implantation coordinates such that the cell activity in the target brain region cannot be observed thus resulting in failure of the experiment. Third, the installation of the fluorescence microscope mount requires adequate precision, and the operation is time-consuming and laborious.

Thus, there is a need to improve this in view of the defects present in the prior art.

SUMMARY

In view of the above, the present application proposes a miniature single-photon fluorescence microscope implantation device and implantation method, which solve or at least partially solve the technical defects in the prior art.

In order to achieve the above purpose, in a first aspect, the present application provides a miniature single-photon fluorescence microscope implantation device, including:

a clamp base, in which a clamp slot is defined, and the clamp slot matches the fluorescence microscope;

a clamp block, matching the clamp slot, and where the clamp block can be clamped in the clamp slot;

wherein a groove is provided in a bottom surface of the clamp slot, and a first protrusion matching the groove is disposed at an end of the clamp block, and the heights of the groove and the first protrusion are both 0.48-0.52 mm, the bottom surface of the groove vertically defines a through receiving hole used to clamp the lens, where the bottom surface of the groove and the bottom surface of the clamp slot outside the groove are parallel to each other.

A miniature single-photon fluorescence microscope implantation device, including:

a clamp base, in which a clamp slot is defined, and the clamp slot matches the fluorescence microscope;

a clamp block, matching the clamp slot, and where the clamp block can be clamped in the clamp slot;

wherein a bottom surface of the clamp slot vertically defines a through receiving hole used to clamp the lens, and where an end of the clamp block is provided with a second protrusion matching the receiving hole, the second protrusion can be clamped in the receiving hole, and the height of the second protrusion is 0.48-0.52 mm.

Preferably, in the micro-single-photon fluorescence microscope implantation device, a side wall of the clamp base further defines a screw hole, and when the clamp block is fixed in the slot, a bolt is screwed to the screw hole and abuts against the clamp block.

Preferably, in the miniature single-photon fluorescence microscope implantation device, the heights of the groove and the first protrusion are both 0.5 mm, and the height of the second protrusion is 0.5 mm.

Preferably, in the miniature single-photon fluorescence microscope implantation device, the clamp block includes a first part and a second part located on the first part, where the first part matches the clamp slot, the first part can be clamped in the clamp slot, and a projected area of the second part on a horizontal plane is larger than a projected area of the first part on the horizontal plane.

Preferably, in the miniature single-photon fluorescence microscope implantation device, a sleeve is further disposed on a lower end surface of the clamp base, and the receiving hole is located in the sleeve.

Preferably, in the miniature single-photon fluorescence microscope implantation device, a plurality of fixing blocks are arranged on an outer periphery of the clamp base.

In a second aspect, the present application further provides a miniature single-photon fluorescence microscope implantation method, including the following operations:

providing the miniature single-photon fluorescence microscope implantation device;

placing the clamp block in the clamp slot of the clamp base, so that the first protrusion is clamped in the groove or the second protrusion is clamped in the receiving hole;

inserting a lens into the receiving hole so that the end of the lens abuts against the first protrusion or the second protrusion;

fixing the clamp base on the stereotaxic instrument, referring to the brain atlas to determine location parameters of a target brain region, drilling a hole in the surface of the skull above the target brain region of the experimental animal thus penetrating the skull, and using a stereotaxic method to implant the lens in the skull of the experimental animal, keeping a manipulator of the stereotaxic instrument still after an implanted depth of the lens reaches the target brain region, and applying a photocurable resin to the bottom surface of the clamp base and the surface of the skull of the experimental animal, irradiating the photocurable resin thus fixing the clamp base;

Pulling out the clamp block, and placing the fluorescence microscope in the clamp slot of the clamp base.

Preferably, in the miniature single-photon fluorescence microscope implantation method, after the lens is inserted into the receiving hole, an adhesive is applied to the end of the receiving hole.

Compared with the prior art, the miniature single-photon fluorescence microscope implantation device and implantation method of the present application have the following beneficial effects.

The miniature single-photon fluorescence microscope implantation device and implantation method of the present application use the receiving hole as a clamping tool for the lens, which can prevent damage to the lens and prevent the lens from tilting. In addition, it can ensure that the lens surface is perpendicular to the bottom surface of the clamp slot of the clamp base, and the process of lens leveling is omitted during the implantation process while ensuring the accuracy of the experiment. The present application defines an receiving hole in the clamp base to hold the lens, so that the clamp base and the lens as a whole can be placed in the optimal operation position at one time, and the assembly of all experimental devices can be completed by only one operation, reducing the impact on the animal and ensure the accuracy of experimental results. Further, the receiving hole of the present application is perpendicular to the groove, and the heights of the groove and the first protrusion are both 0.48 to 0.52 mm, so that the surface of the lens could be parallel to the surface of the fluorescence microscope lens without adjusting the lens, and an operating distance of 0.48-0.52 mm is reserved, which greatly improves the operating efficiency.

BRIEF DESCRIPTION OF DRAWINGS

For a clearer understanding of the technical solutions that are used in the embodiments according to the present application or that are used in the related art, hereinafter the drawings that are required for the description of the embodiments disclosed herein or the related art will be briefly introduced. Apparently, the drawings in the following description merely represent some embodiments of the present application, and for those having ordinary skill in the art, other drawings may also be obtained based on these drawings without investing creative efforts.

DETAILED DESCRIPTION OF EMBODIMENTS

Figures 1, 2:
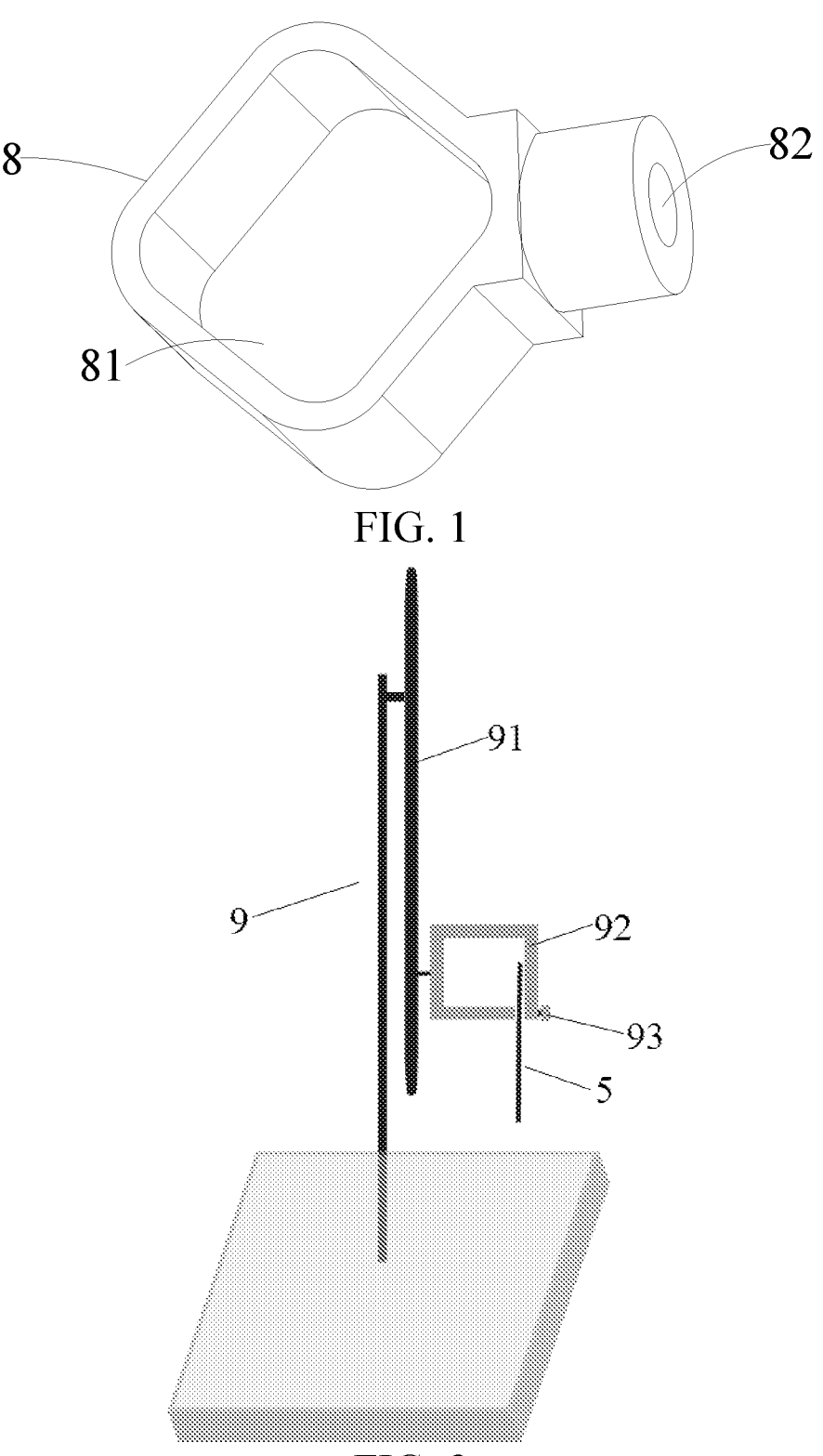
FIG. 1 is a schematic diagram of a fluorescence microscope implantation device in the prior art.
FIG. 2 is a schematic diagram of a stereotaxic instrument clamping a lens in the prior art.

Embodiments of the present application will be described in detail below, examples of which are shown in the drawings, where the same or similar reference numerals denote the same or similar elements or elements having the same or similar functions throughout. The embodiments described below by referring to the drawings are merely exemplary for purposes explaining the present application, and are not to be construed as limiting the present application.

As illustrated in FIGS. 5 to 10, embodiments of the present application provide a miniature single-photon fluorescence microscope implantation device, including:

a clamp base 1, defining a clamp slot 11 matching a fluorescence microscope; and a clamp block 2, matching the clamp slot 11, where the clamp block 2 can be clamped in the clamp slot 11;

where there is a groove 12 in a bottom surface of the clamp slot 11, and an end of the clamp block 2 includes a first protrusion 3 matching the groove 12; heights of the groove 12 and the first protrusion 3 both lie in the range of 0.48 to 0.52 mm; a bottom of the groove 12 is vertically provided with a through receiving hole 4, which is used to clamp a lens 5; the bottom surface of the groove 12 is parallel to the bottom surface of the clamp slot 11 outside the groove 12.

The miniature single-photon fluorescence microscope implantation device provided in the embodiments of the present application includes a clamp base 1 and a clamp block 2. There is defined a clamp slot 11 in the clamp base 1, where the clamp slot 11 matches the fluorescence microscope (specifically, the lens of the fluorescence microscope), which can be clamped in the clamp slot 11. The clamp block 2 may also be clamped in the clamp slot 11. That is, the clamp block 2 has exactly the same shape as the fluorescence microscope. A groove 12 is defined in the bottom of the clamp slot 11. Correspondingly, a first protrusion 3 is arranged at an end of the clamp block 2, where the first protrusion 3 fits into and can be clamped in the groove 12. The heights of the groove 12 and the first protrusion 3 both lie in the range of 0.48 to 0.52 mm. Furthermore, a receiving hole 4 is vertically defined in the bottom of the groove 12, where the receiving hole 4 matches the lens 5 and is used to clamp the lens 5. The bottom surface of the groove 12 and the bottom surface of the clamp slot 11 outside the groove 12 are parallel to each other. When in use, the clamp block 2 is first clamped in the clamp slot 11, and the first protrusion 3 is made to be clamped in the groove 12. Then the lens 5 is inserted into the receiving hole 4, the end of the lens 5 is made to abut against the lower end surface of the first protrusion 3. At this time, the upper end surface of the lens 5 and the lower end surface of the first protrusion 3 are parallel to each other. Then, the clamp block 2 is pulled out, and the fluorescence microscope lens is fully inserted into the clamp slot 11. At this time, the surface of the lens 5 is parallel to the lens surface of the fluorescence microscope, and the gap between the lens 5 and the fluorescence microscope lies in the range of 0.48 to 0.52 mm.

In particular, FIG. 1 shows the fluorescence microscope implantation device of Thinker Tech in the prior art, the fluorescence microscope implantation device including a microscope mounting seat 8. The mounting seat 8 defines a mounting hole 81, and the fluorescence microscope can be clamped in the mounting hole 81. In addition, a side wall of the mounting seat 8 has a screw hole 82. After the fluorescence microscope is clamped in the mounting hole 81, a bolt is screwed into the screw hole 82 to press against the fluorescence microscope so that the fluorescence microscope is stably clamped in the mounting seat 8.

FIG. 2 shows a schematic diagram of a stereotaxic instrument clamping a lens in the prior art. In particular, in the stereotaxic instrument 9 in FIG. 2, the joystick 91 is installed on the stereotaxic instrument 9. In application, the resin frame 92 is first installed on the joystick 91, then the lens 5 is placed in the mounting hole in the resin frame 92, and then the screw 93 is used to fasten the lens 5, thereby realizing the clamping of the lens by the stereotaxic instrument.

Figures 3, 4:
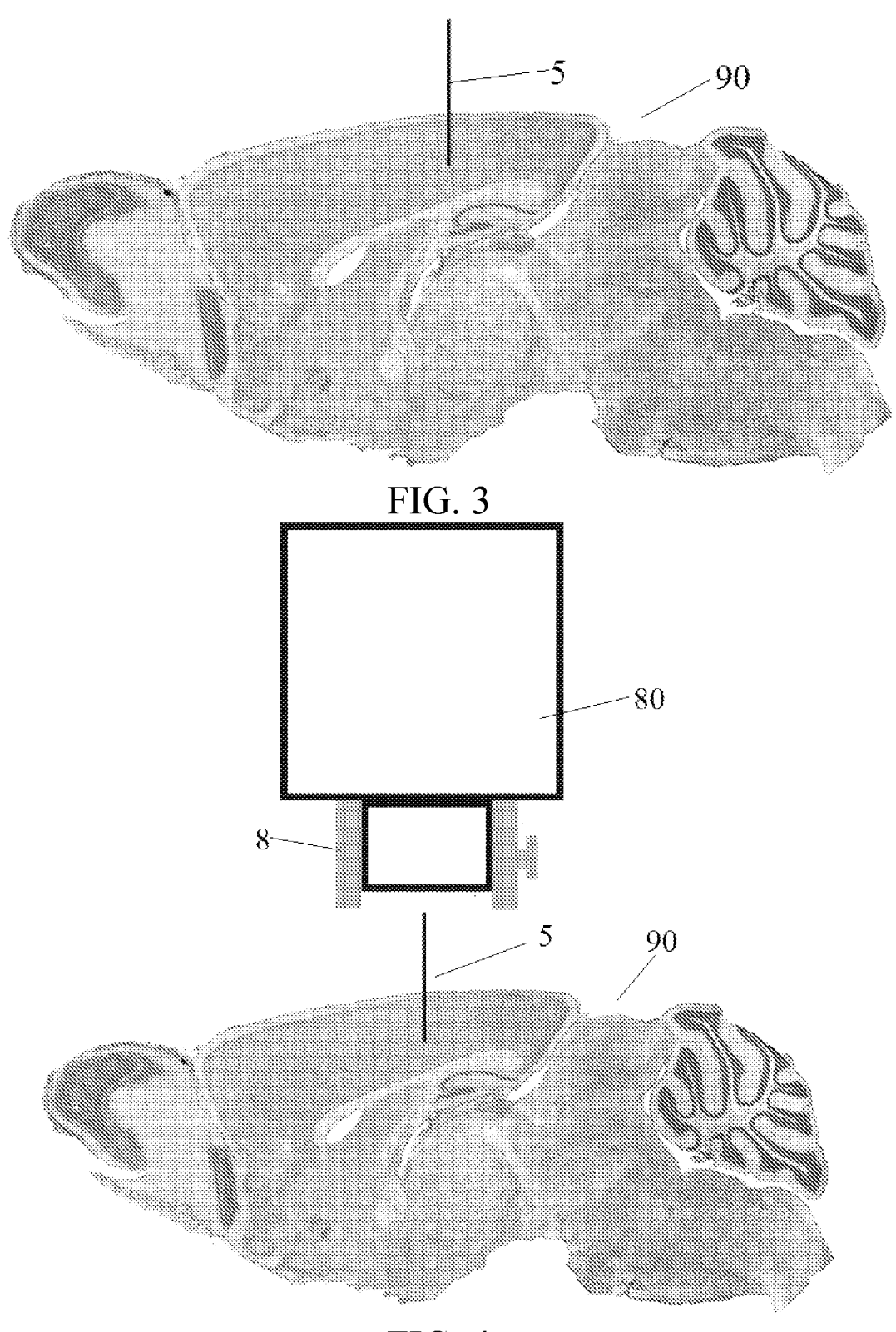
FIG. 3 is a schematic diagram of a lens being implanted in a target brain region of the experimental animal in the prior art.
FIG. 4 is a schematic diagram of adjusting the fluorescence microscope and the mounting seat to an appropriate position in the prior art.
Figure 5:
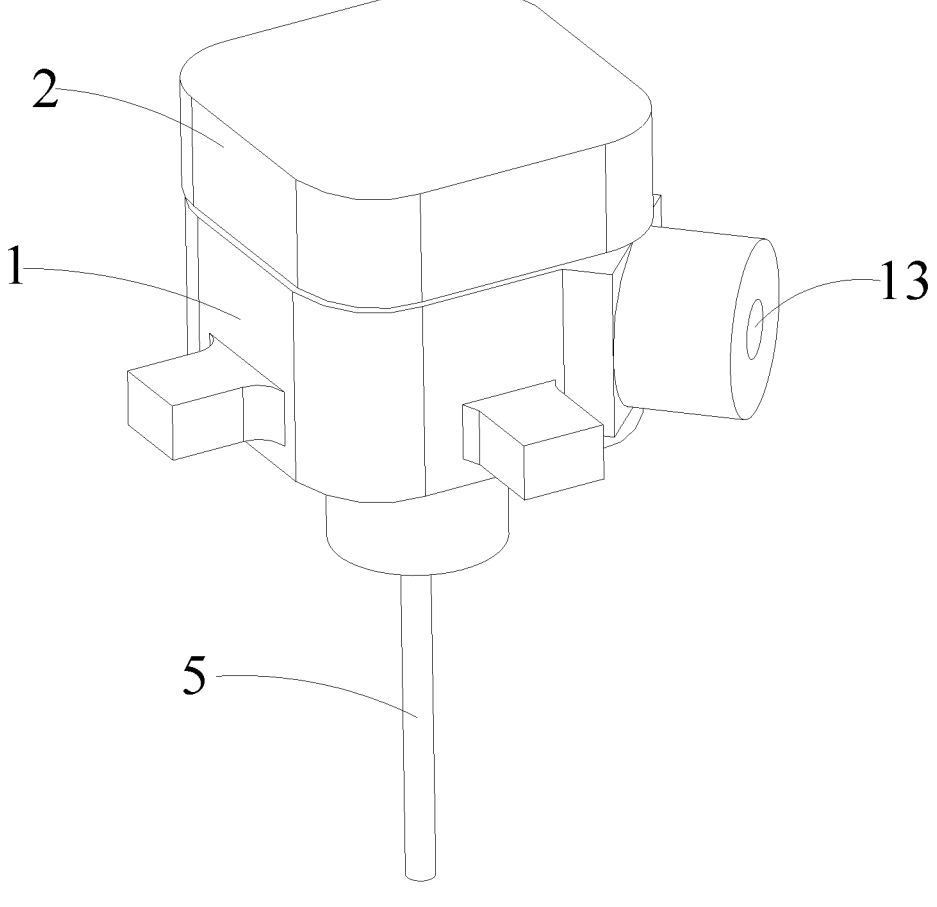
FIG. 5 is a schematic diagram of a single-photon fluorescence microscope implantation device according to an embodiment of the present application.
Figures 6, 7:
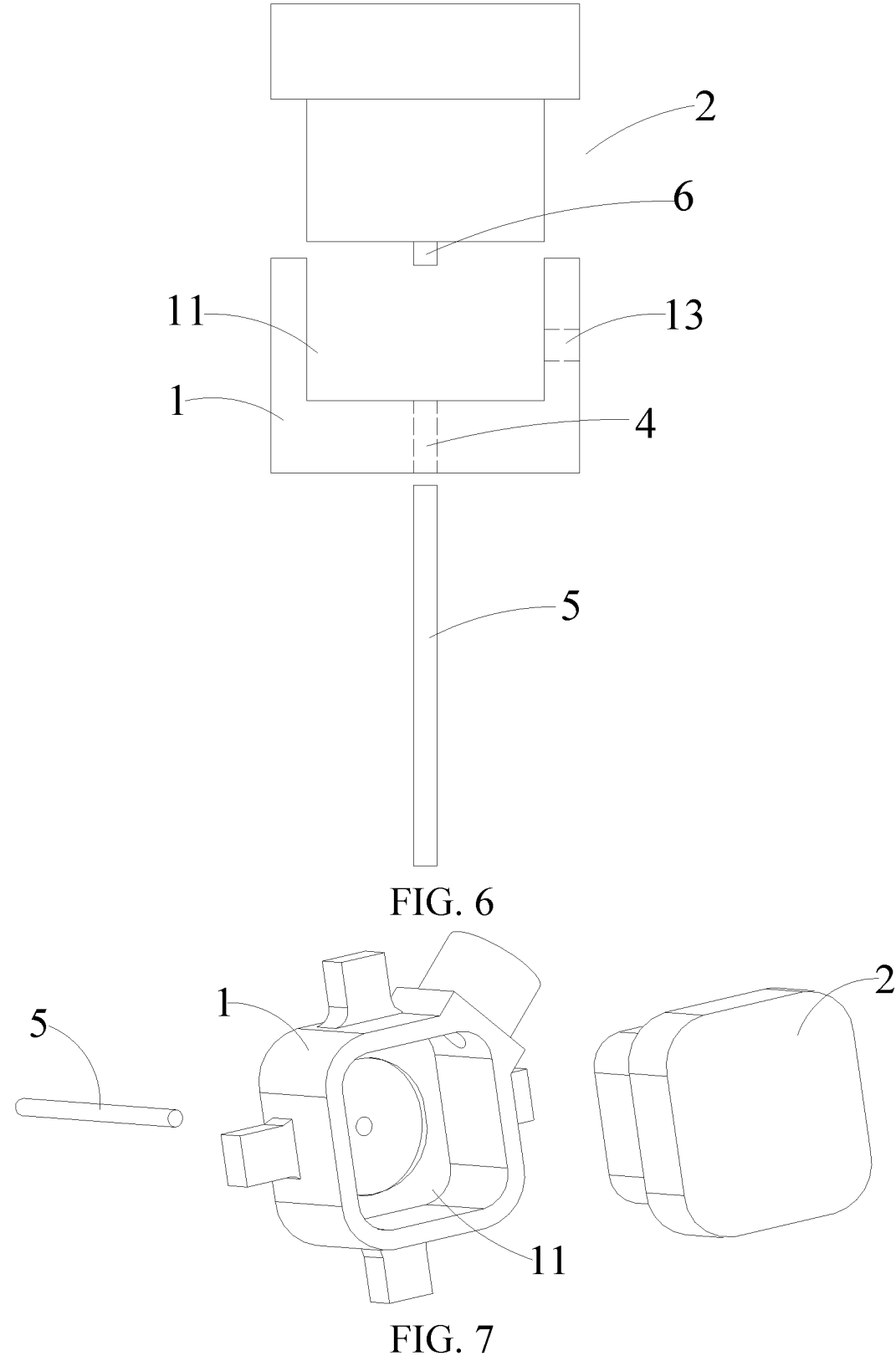
FIG. 6 is a schematic diagram of a single-photon fluorescence microscope implantation device according to an embodiment of the present application.
FIG. 7 is a schematic diagram of a clamp base, a clamp block, and a lens in according to an embodiment of the present application.
Figure 8:
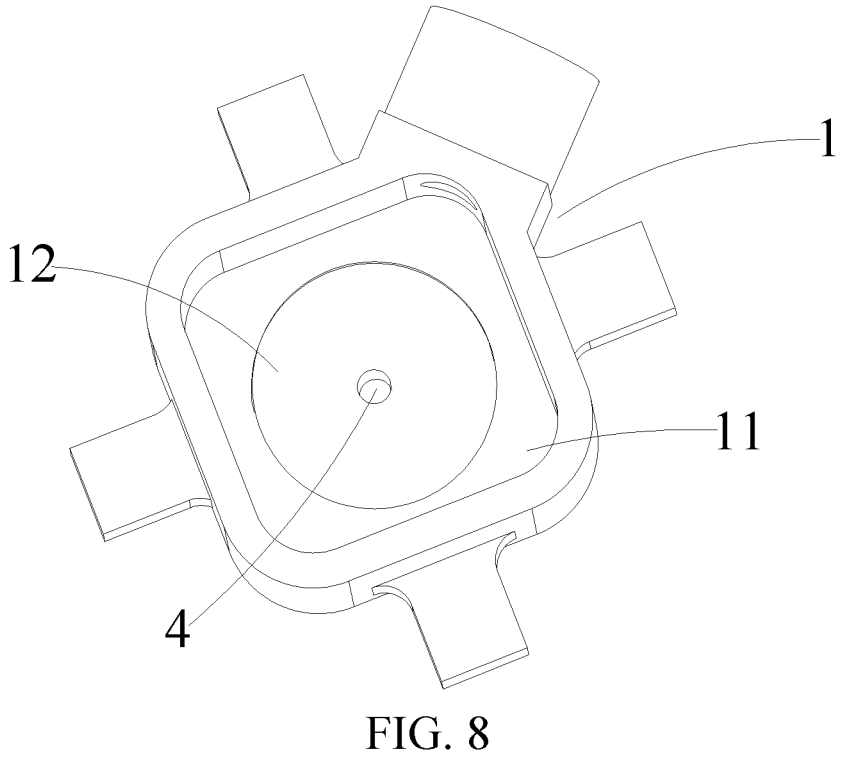
FIG. 8 is a schematic view of a clamp base according to an embodiment of the present application.
Figure 9:
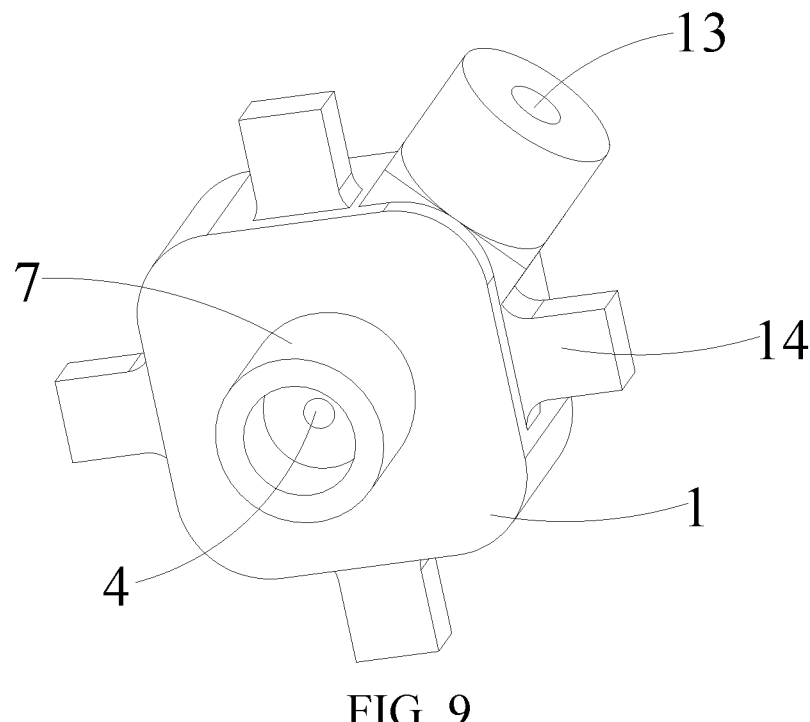
FIG. 9 is a side view of a clamp base according to an embodiment of the present application.

When in use, the brain atlas is referred to determine the location parameters of the target brain region of the experimental animal, a hole is drilled in the surface of the skull above the target brain region to penetrate the skull, and the lens is implanted in the skull of the experimental animal using a stereotaxic instrument holding the lens through a conventional stereotaxic method. As illustrated in FIG. 3, the lens 5 is implanted in the target brain region 90 of the experimental animal. At this time, one end of the lens 5 is embedded in the target brain region 90, and the other end is exposed outside the skull, where certain protective measures are taken. After the virus has been fully expressed, fluorescence can be seen in the target brain region. As shown in FIG. 4, after inserting the lens portion of the fluorescence microscope 80 into the mounting hole 81 in the mounting seat 8, a bolt is used for fastening. At this time, the fluorescence microscope 80 and the mounting seat 8 are integrated, which is collectively called an assembly. Then the assembly is gripped using a gripping tool, and when the assembly and lens are in place, fluorescence will appear in the field of view. Then the position of the assembly can be properly adjusted depending on the clarity of the fluorescence in the field of view. When the lens plane of the fluorescence microscope 80 is absolutely parallel to the cylindrical lens plane and the gap between the lens plane of the fluorescence microscope 80 and the cylindrical lens plane reaches 0.5 mm, it indicates the proper position is reached. Then immediately fix the mounting seat 8 on the surface of the skull, loosen the fixing bolt, and take out the fluorescence microscope 80. As such, the optimal field of view can be obtained by inserting the fluorescence microscope 80 into the mounting hole 81 during the experiment.

Comparing the present application against the prior art, the miniature single-photon fluorescence microscope implantation device of the present application uses the receiving hole as a clamping tool for the lens, which can avoid damage to the lens and prevent the lens from tilting. In addition, the lens surface can be ensured to be perpendicular to the bottom surface of the clamp slot of the clamp base, and the process of lens leveling is eliminated during the implantation process while ensuring the accuracy of the experiment. The present application defines an receiving hole in the clamp base to hold the lens, so that the clamp base and the lens as a whole can be placed in the optimal operating position at one time, and the assembly of all experimental devices can be completed by only one operation, reducing the impact on the animal and ensure the accuracy of experimental results. Further, the receiving hole of the present application is perpendicular to the groove, and the heights of the groove and the first protrusion are both 0.48 to 0.52 mm, so that the surface of the lens 5 could be parallel to the surface of the fluorescence microscope lens without needing to adjust the lens, and a working distance of 0.48-0.52 mm is left, which greatly improves the operating efficiency.

In some embodiments, referring to FIG. 6 again, a miniature single-photon fluorescence microscope implantation device includes:

a clamp base 1, defining a clamp slot 11 matching a fluorescence microscope;

a clamp block 2, matching the clamp slot 11, where the clamp block 2 can be clamped in the clamp slot 11;

where a bottom surface of the slot 11 is vertically provided with a through receiving hole 4 used to clamp the lens 5, and an end of the clamp block 2 includes a second protrusion 6 matching the receiving hole 4; the second protrusion 6 can be clamped in the receiving hole 4, and the height of the second protrusion 6 lies in the range of 0.48-0.52 mm.

In the above embodiment, the receiving hole 4 is directly opened in the bottom of the clamp slot 11, and the corresponding end of the clamp block 2 includes a second protrusion 6 matching the receiving hole 4. The height of the second protrusion 6 lies in the range of 0.48 to 0.52 mm, and can be clamped in the receiving hole 4. When in use, the clamp block 2 is first inserted into the clamp slot 11 making the second protrusion 6 fully clamped on one end of the receiving hole 4, then the lens 5 is inserted into the other end of the receiving hole 4 making the end of the lens 5 abut against the lower end surface of the second protrusion 6. At this time, the lens 5 is perpendicular to the second protrusion 6. Then, the clamp block 2 is pulled out, and the fluorescence microscope (specifically, the lens portion of the microscope) is completely inserted into the clamp slot 11. At this time, the surface of the lens 5 is parallel to the lens surface of the fluorescence microscope, and the gap between the lens 5 and the fluorescence microscope lies in the range of 0.48 to 0.52 mm.

In some embodiments, the side wall of the clamp base 1 further defines a screw hole 13. When the clamp block 2 is clamped in the clamp slot 11, a bolt is screwed into the screw hole 13 and abuts against the clamp block 2.

In the above embodiment, a screw hole 13 is provided in the side wall of the clamp base 1. When the clamp block 2 is clamped in the clamp slot 11, the bolt is screwed into the screw hole 13, and the bolt abuts against only the clamp block 2, so that the clamp block 2 can be more stably clamped inside the clamp slot 11.

In some embodiments, the heights of the groove 12 and the first protrusion 3 are both 0.5 mm, and the height of the second protrusion 6 is 0.5 mm. In particular, the first protrusion 3 may be a cylindrical protrusion with a diameter of 3.7 mm.

In the above embodiments, the heights of the groove 12 and the first protrusion 3 are both 0.5 mm, and the height of the second protrusion 6 is 0.5 mm, thus ensuring that the gap between the lens 5 and the fluorescence microscope is 0.5 mm, which is conducive to carrying out experiments.

In some embodiments, the clamp block 2 includes a first part 21 and a second part 22 located on the first part 21. The first part 21 matches the clamp slot 11, and can be clamped in the clamp slot 11. A projected area of the second portion

22 on a horizontal plane is larger than a projected area of the first portion 21 on the horizontal plane.

In the above embodiments, the clamp block 2 includes a first part 21 and a second part 22. When in use, the first part 21 is clamped in the clamp slot 11, while the second part is exposed outside the clamp slot 11. The projected area of the second part 22 on the horizontal plane is larger than the projected area of the first part 21 on the horizontal plane, so that the clamp block 2 can be easily pulled out from the clamp slot 11 through the second part 22.

In some embodiments, a sleeve 7 is disposed on the lower surface of the clamp base 1, and the receiving hole 4 is located in the sleeve 7. By setting the sleeve 7 on the lower end surface of the clamp base 1 and on the outer periphery of the receiving hole 4. When the lens 5 is inserted into the receiving hole 4, an adhesive may be applied in the sleeve 7 at the port of the receiving hole 4, so that the lens 5 can be more stably clamped in the receiving hole 4.

In some embodiments, a plurality of fixing blocks 14 are further disposed on an outer periphery of the clamp base 1. By arranging the plurality of fixing blocks 14, when the clamp base 1 is fixed on the surface of the skull of the experimental animal, the contact area is increased thus enhancing firmness.

Based on the same inventive concept, embodiments of the present application further provide a miniature single-photon fluorescence microscope implantation method, including the following operations:

S1: Providing the above-mentioned miniature single-photon fluorescence microscope implantation device;

S2: Placing the clamp block in the clamp slot of the clamp base, so that the first protrusion is clamped in the groove or the second protrusion is clamped in the receiving hole;

S3: Inserting the lens into the receiving hole so that the end of the lens abuts against the first protrusion or the second protrusion;

S4: Then fixing the clamp base on the stereotaxic instrument, referring to the brain atlas to determine location parameters of a target brain region, drilling a hole in a surface of the skull above the target brain region of the experimental animal thus penetrating the skull, and using the stereotaxic method to implant the lens into the skull of the experimental animal; after the implanted depth of the lens reaches the target brain region, keeping a manipulator arm of the stereotaxic instrument still, and applying a photocurable resin to the bottom of the clamp base and the surface of the skull of the experimental animal, then irradiating the clamp base to realize fixing;

S5: Pulling out the clamp block, and placing the fluorescence microscope in the clamp slot of the clamp base.

In some embodiments, after the lens is inserted into the receiving hole, an adhesive is applied to the end of the receiving hole.

Specifically, experimental animals include but are not limited to mice.

Figures 10, 11:
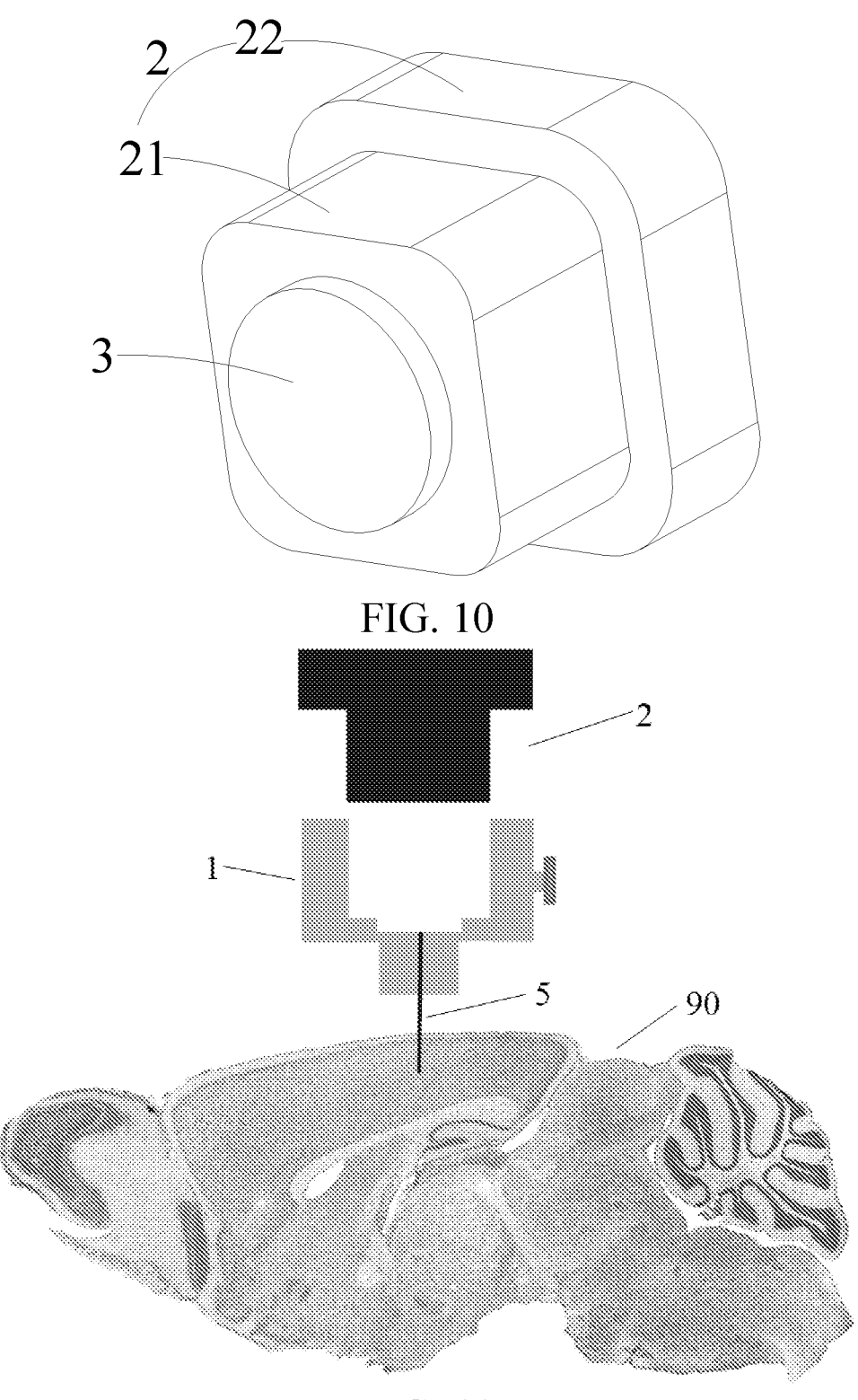
FIG. 10 is a schematic view of a clamp block according to an embodiment of the present application.
FIGS. 11-12 are schematic diagrams of a miniature single-photon fluorescence microscope implantation method according to an embodiment of the present application.
Figure 12:
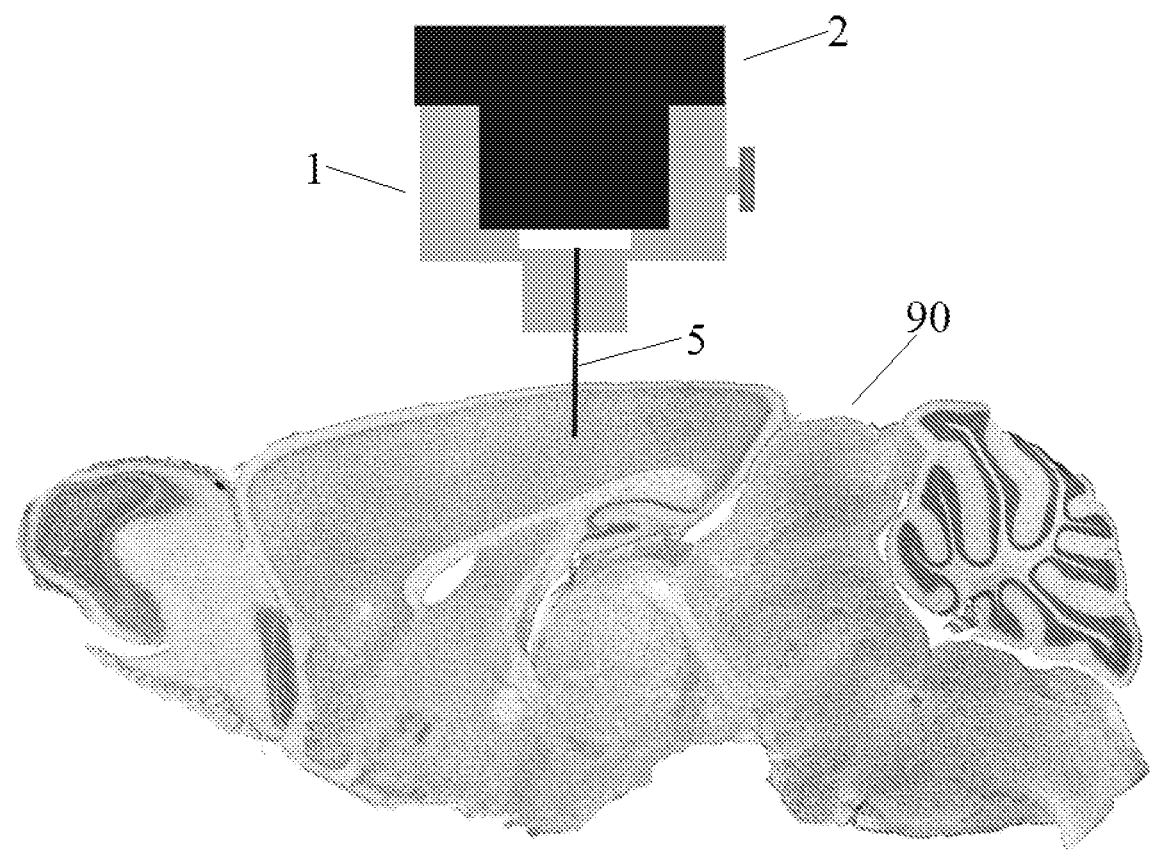

In particular, referring to FIGS. 11~12. Place the clamp block 2 in the clamp slot of the clamp base 1, and make the first protrusion 3 at the lower end of the clamp block 2 completely fit in the groove 12, and then screw a bolt into the screw hole 13 opened in the side wall of the clamp base 1 to abut against the clamp block 2 thus making the clamp block 2 more stable. Then insert the lens 5 into the receiving hole 4, and apply an adhesive (such as soft glue) on the port of the receiving hole 4 so that the lens 5 is more firmly installed in the receiving hole 4. Then the lens 5, the clamp block 2, and the clamp base 1 are fixed on the stereotaxic instrument as a whole. Referring to the brain atlas to determine the location parameters of the target brain region. Drill a hole in the surface of the skull above the target brain region of the experimental animal thus penetrating the skull. Using the stereotaxic method, the lens is implanted in the skull of the experimental animal. After the lens implantation depth reaches the target brain region, keep the manipulator arm of the stereotaxic instrument still, apply a photocurable resin on the bottom of the clamp base and the surface of the skull of the experimental animal, and cure the resin after a certain period of irradiation, so that the clamp base 1 is fixed at the current position. At this time, one end face of the lens 5 is located in the target brain region, and the other end face is located in the receiving hole 4 of the clamp base 1. The end face of the lens 5 is parallel to the bottom surface of the clamp slot 11 and contacts the lower surface of the first protrusion 3 at the lower end of the clamp block 2. Then loosen the bolt in the side wall of the clamp base 1, and pull out the clamp block 2. Then insert the fluorescence micro-scope lens into the clamp slot 11. At this time, there is an operating distance of 0.48-0.52 mm between the surface of the microscope lens and the surface of the cylindrical lens, and the surface of the microscope lens and the surface of the lens 5 are parallel to each other; at this time, the imaging experiment can be started.

The foregoing merely portrays some embodiments of the present application. Those of ordinary skill in the art will be able to make numerous improvements and modifications without departing from the principle of this application, and these improvements and modifications should all be regarded as falling in the scope of protection of this appli-cation.

What is claimed is:

1. A miniature single-photon fluorescence microscope implantation device, comprising:
   a clamp base, comprising a clamp slot, the clamp slot matching the fluorescence microscope;
   a clamp block, matching the clamp slot and operative to be clamped in the clamp slot;
   wherein a groove is defined in a bottom surface of the clamp slot, and an end of the clamp block comprises a first protrusion matching the groove; wherein heights of the groove and the first protrusion both lie in the range of 0.48 to 0.52 mm; wherein a bottom surface of the groove vertically defines a through receiving hole used to clamp a lens; wherein the bottom surface of the groove is parallel to the bottom surface of the clamp slot outside the groove.

2. The miniature single-photon fluorescence microscope implantation device as recited in claim 1, wherein a side wall of the clamp base further defines a screw hole; and wherein when the clamp block is fixed to the groove, a bolt is screwed into the screw hole to abut against the clamp block.

3. The miniature single-photon fluorescence microscope implantation device as recited in claim 1, wherein a height of the groove and a height of the first protrusion are each 0.5 mm, and a height of the second protrusion is 0.5 mm.

4. The miniature single-photon fluorescence microscope implantation device as recited in claim 1, wherein the clamp block comprises a first part and a second part disposed on the first part, wherein the first part matches the clamp slot and is operative to be clamped in the clamp slot; and wherein a projected area of the second part on a horizontal plane is larger than a projected area of the first part on the horizontal plane.

5. The miniature single-photon fluorescence microscope implantation device as recited in claim 1, wherein a sleeve is disposed on a lower surface of the clamp base, and the receiving hole is located in the sleeve.

6. The miniature single-photon fluorescence microscope implantation device as recited in claim 1, wherein a plurality of fixing blocks are arranged on a periphery of the clamp base.

7. A miniature single-photon fluorescence microscope implantation method, comprising:
   providing the miniature single-photon fluorescence microscope implantation device as recited in claim 1;
   placing the clamp block in the clamp slot of the clamp base, so that the first protrusion is clamped in the groove;
   inserting the lens into the receiving hole so that the end of the lens abuts against the first protrusion;
   fixing the clamp base on a stereotaxic instrument, refer-ring to a brain atlas and determining location param-eters of a target brain region, drilling a hole in a surface of a skull above the target brain region of an experi-mental animal thus penetrating the skull, and using a stereotaxic method to implant the lens in the skull of the experimental animal, keeping a manipulator of the stereotaxic instrument still after an implanted depth of the lens reaches the target brain region, and applying a photocurable resin to the bottom surface of the clamp base and a surface of the skull of the experimental animal, and irradiating the photocurable resin thus fixing the clamp base; and
   pulling out the clamp block, and placing the fluorescence microscope in the clamp slot of the clamp base.

8. The miniature single-photon fluorescence microscope implantation method as recited in claim 7, wherein after the lens is inserted into the receiving hole, an adhesive is applied to an end of the receiving hole.

9. A miniature single-photon fluorescence microscope implantation device, comprising:
   a clamp base, comprising a clamp slot, the clamp slot matching the fluorescence microscope;
   a clamp block, matching the clamp slot and operative to be clamped in the clamp slot;
   wherein a bottom surface of the clamp slot vertically defines a through receiving hole used to clamp a lens, and end of the clamp block comprises a second pro-trusion matching the receiving hole, wherein the sec-ond protrusion is operative to be clamped in the receiv-ing hole, and wherein a height of the second protrusion lies in the range of 0.48 to 0.52 mm.

10. The miniature single-photon fluorescence microscope implantation device as recited in claim 9, wherein a side wall of the clamp base further defines a screw hole; and wherein when the clamp block is fixed to the groove, a bolt is screwed into the screw hole to abut against the clamp block.

11. The miniature single-photon fluorescence microscope implantation device as recited in claim 9, wherein a height of the groove and a height of the first protrusion are each 0.5 mm, and a height of the second protrusion is 0.5 mm.

12. The miniature single-photon fluorescence microscope implantation device as recited in claim 9, wherein the clamp block comprises a first part and a second part disposed on the first part, wherein the first part matches the clamp slot and is operative to be clamped in the clamp slot; and wherein a projected area of the second part on a horizontal plane is larger than a projected area of the first part on the horizontal plane.

13. The miniature single-photon fluorescence microscope implantation device as recited in claim 9, wherein a sleeve is disposed on a lower surface of the clamp base, and the receiving hole is located in the sleeve.

14. The miniature single-photon fluorescence microscope implantation device as recited in claim 9, wherein a plurality of fixing blocks are arranged on a periphery of the clamp base.

15. A miniature single-photon fluorescence microscope implantation method, comprising:

providing the miniature single-photon fluorescence microscope implantation device as recited in claim 9;

placing the clamp block in the clamp slot of the clamp base, so that the second protrusion is clamped in the receiving hole;

inserting the lens into the receiving hole so that the end of the lens abuts against the second protrusion;

fixing the clamp base on a stereotaxic instrument, referring to a brain atlas and determining location parameters of a target brain region, drilling a hole in a surface of a skull above the target brain region of an experimental animal thus penetrating the skull, and using a stereotaxic method to implant the lens in the skull of the experimental animal, keeping a manipulator of the stereotaxic instrument still after an implanted depth of the lens reaches the target brain region, and applying a photocurable resin to the bottom surface of the clamp base and a surface of the skull of the experimental animal, and irradiating the photocurable resin thus fixing the clamp base; and pulling out the clamp block, and placing the fluorescence microscope in the clamp slot of the clamp base.

16. The miniature single-photon fluorescence microscope implantation method as recited in claim 15, wherein after the lens is inserted into the receiving hole, an adhesive is applied to an end of the receiving hole.

\* \* \* \* \*